(12) United States Patent
Thibaud

(10) Patent No.: US 10,286,353 B2
(45) Date of Patent: May 14, 2019

(54) OXYGEN SENSOR PROTECTION

(71) Applicant: Hamilton Sundstrand Corporation, Charlotte, NC (US)

(72) Inventor: Catherine Thibaud, South Windsor, CT (US)

(73) Assignee: Hamilton Sundstrand Corporation, Charlotte, NC (US)

( * ) Notice: Subject to any disclaimer, the term of this patent is extended or adjusted under 35 U.S.C. 154(b) by 0 days.

(21) Appl. No.: 16/015,432

(22) Filed: Jun. 22, 2018

(65) Prior Publication Data

US 2018/0296968 A1 Oct. 18, 2018

Related U.S. Application Data

(62) Division of application No. 14/799,121, filed on Jul. 14, 2015, now Pat. No. 10,022,663.

(51) Int. Cl.
*B01D 53/02* (2006.01)
*B01D 53/04* (2006.01)
(Continued)

(52) U.S. Cl.
CPC ............ *B01D 53/0415* (2013.01); *A62C 3/08* (2013.01); *A62C 99/0018* (2013.01); *B01D 53/0407* (2013.01); *B01D 53/0446* (2013.01); *B01D 53/22* (2013.01); *B01D 53/30* (2013.01); *B64D 37/32* (2013.01); *G01N 33/0014* (2013.01); *G01N 33/0036* (2013.01); *B01D 2253/102* (2013.01); *B01D 2253/25* (2013.01); *B01D 2256/10* (2013.01); *B01D 2257/104* (2013.01); *B01D 2257/553* (2013.01);
(Continued)

(58) Field of Classification Search
CPC ................ A62C 3/08; B01D 2253/102; B01D 2253/25; B01D 2257/104; B01D 2257/553; B01D 2257/556; B01D 2259/401; B01D 2259/4575; B01D 53/0407; B01D 53/0415; B01D 53/0446; B01D 53/22; B01D 53/30; B64D 37/32
See application file for complete search history.

(56) References Cited

U.S. PATENT DOCUMENTS

| 4,759,210 A | 7/1988 | Wohltjen |
| 4,911,892 A | 3/1990 | Grace et al. |

(Continued)

FOREIGN PATENT DOCUMENTS

| JP | 2047546 A | 2/1990 |
| JP | 4164244 A | 6/1992 |
| WO | WO0173418 A2 | 10/2001 |

OTHER PUBLICATIONS

Extended European Search Report for EP Application No. 16179450. 8, dated Dec. 20, 2016, 8 Pages.

*Primary Examiner* — Christopher P Jones
(74) *Attorney, Agent, or Firm* — Kinney & Lange, P.A.

(57) ABSTRACT

An air separation system includes an air separation module configured to receive feed air and separate the feed air into nitrogen-enriched air and oxygen-enriched air, a nitrogen-enriched air line for transporting the nitrogen-enriched air from the air separation module to a fuel tank for inerting, an oxygen sensing line connected to the nitrogen-enriched air line, a gas adsorption filter located in the oxygen sensing line, and an oxygen sensor downstream of the gas adsorption filter in the oxygen sensing line.

12 Claims, 2 Drawing Sheets

(51) Int. Cl.
   *A62C 3/08*   (2006.01)
   *B01D 53/22*  (2006.01)
   *B01D 53/30*  (2006.01)
   *B64D 37/32*  (2006.01)
   *G01N 33/00*  (2006.01)
   *A62C 99/00*  (2010.01)

(52) U.S. Cl.
   CPC .. *B01D 2257/556* (2013.01); *B01D 2259/401* (2013.01); *B01D 2259/4575* (2013.01)

(56) References Cited

U.S. PATENT DOCUMENTS

| | | | |
|---|---|---|---|
| 6,036,829 A | 3/2000 | Yamada et al. | |
| 6,365,108 B1 | 4/2002 | Philyaw | |
| 6,630,062 B1 | 10/2003 | Anderson et al. | |
| 7,254,985 B2 | 8/2007 | Isomura et al. | |
| 7,753,034 B2* | 7/2010 | Hoke | B01D 53/02 123/518 |
| 8,176,767 B2 | 5/2012 | Schneider et al. | |
| 8,667,977 B1 | 3/2014 | McCaul et al. | |
| 8,833,141 B2 | 9/2014 | Wolst et al. | |
| 2001/0031886 A1* | 10/2001 | Okawa | C07F 7/0885 556/467 |
| 2004/0226438 A1 | 11/2004 | Jones | |
| 2005/0092176 A1 | 5/2005 | Ding et al. | |
| 2005/0229968 A1 | 10/2005 | Jones et al. | |
| 2005/0247197 A1* | 11/2005 | Snow, Jr. | A62C 3/06 95/138 |
| 2005/0286054 A1* | 12/2005 | Chen | G01N 21/3504 356/437 |
| 2007/0068386 A1* | 3/2007 | Mitariten | B01D 53/04 95/116 |
| 2008/0148815 A1* | 6/2008 | Lucas | G01N 30/08 73/23.41 |
| 2008/0314246 A1* | 12/2008 | Deckman | B01D 53/02 95/130 |
| 2011/0247620 A1* | 10/2011 | Armstrong | B01D 53/047 128/204.23 |
| 2013/0192463 A1* | 8/2013 | Wu | G01N 1/2205 95/82 |
| 2014/0157986 A1* | 6/2014 | Ravikovitch | B01D 53/04 95/96 |
| 2014/0171304 A1 | 6/2014 | Herrera et al. | |
| 2014/0208943 A1* | 7/2014 | Gupta | B64D 37/32 95/14 |
| 2015/0023844 A1* | 1/2015 | Clayton, Jr. | F01N 3/035 422/169 |

* cited by examiner

OXYGEN SENSOR PROTECTION

CROSS-REFERENCE TO RELATED APPLICATION(S)

This application is a divisional of U.S. application Ser. No. 14/799,121 filed Jul. 14, 2015 for "OXYGEN SENSOR PROTECTION" by C. Thibaud.

BACKGROUND

This disclosure relates to air separation systems for aircraft, and more specifically to an oxygen sensor for a nitrogen generation system.

Aircraft fuel tanks and containers can contain potentially combustible combinations of oxygen, fuel vapors, and ignition sources. In order to prevent combustion, the ullage of fuel tanks and containers is filled with air with high nitrogen concentration, or nitrogen-enriched air (NEA). A nitrogen generation system (NGS) is commonly used to produce NEA for inerting fuel tanks and containers. An air separation module (ASM) in the NGS separates ambient air into NEA, which is directed to fuel tanks and containers, and oxygen-enriched air (OEA), which is rejected overboard. For a given system, the amount of oxygen in the NEA depends on various parameters such as feed flow and operating pressure. Therefore, an oxygen sensor can be used to ensure that the oxygen concentration in the NEA remains below a prescribed level in order to reduce risk of explosion in fuel tanks and containers.

However, oxygen sensors can be susceptible to premature failure due to contamination with siloxane compounds. Siloxane compounds can form silicon dioxide films on top of an oxygen sensor that prevent oxygen from diffusing through the layers of the sensor. As a result, the sensor does not accurately measure the oxygen concentration in the NEA produced by the ASM and requires replacement. Siloxane compounds can be released by various types of sealants used in aircraft. Siloxane compounds are also used in various personal care products, such as shampoos and deodorants, so siloxane compounds can be abundant in ambient air present in aircraft, particularly in aircraft cabins. Even small amounts of siloxane compounds (on the level of parts per billion) can affect the performance of an oxygen sensor.

SUMMARY

In one embodiment, an air separation system includes an air separation module configured to receive feed air and separate the feed air into nitrogen-enriched air and oxygen-enriched air, a nitrogen-enriched air line for transporting the nitrogen-enriched air from the air separation module to a fuel tank for inerting, an oxygen sensing line connected to the nitrogen-enriched air line, a gas adsorption filter located in the oxygen sensing line, and an oxygen sensor downstream of the gas adsorption filter in the oxygen sensing line.

In another embodiment, an oxygen sensor protection system includes an oxygen sensing line, a gas adsorption filter located in the oxygen sensing line, and an oxygen sensor downstream of the gas adsorption filter in the oxygen sensing line.

In another embodiment a method for protecting an oxygen sensor from siloxane compounds includes flowing air through an oxygen sensing line, filtering the air with a sorbent to adsorb siloxane compounds in the air, and flowing the air through an oxygen sensor to sense a concentration of oxygen in the air.

DETAILED DESCRIPTION

The present disclosure relates to an air separation system, specifically a nitrogen generation system (NGS), for generating air with high nitrogen concentration (nitrogen-enriched air). An air separation module (ASM) in the NGS separates feed air into nitrogen-enriched air (NEA) and oxygen-enriched air (OEA). The oxygen concentration in the NEA is measured using an oxygen sensor to ensure that the oxygen concentration in the NEA remains below a prescribed level. The NGS includes a gas adsorption filter for protecting the oxygen sensor from premature failure due to exposure to siloxane compounds. The gas adsorption filter adsorbs any siloxane compounds in the NEA and prevents silicon dioxide films from forming on the oxygen sensor and causing the oxygen sensor to fail.

Figure 1:
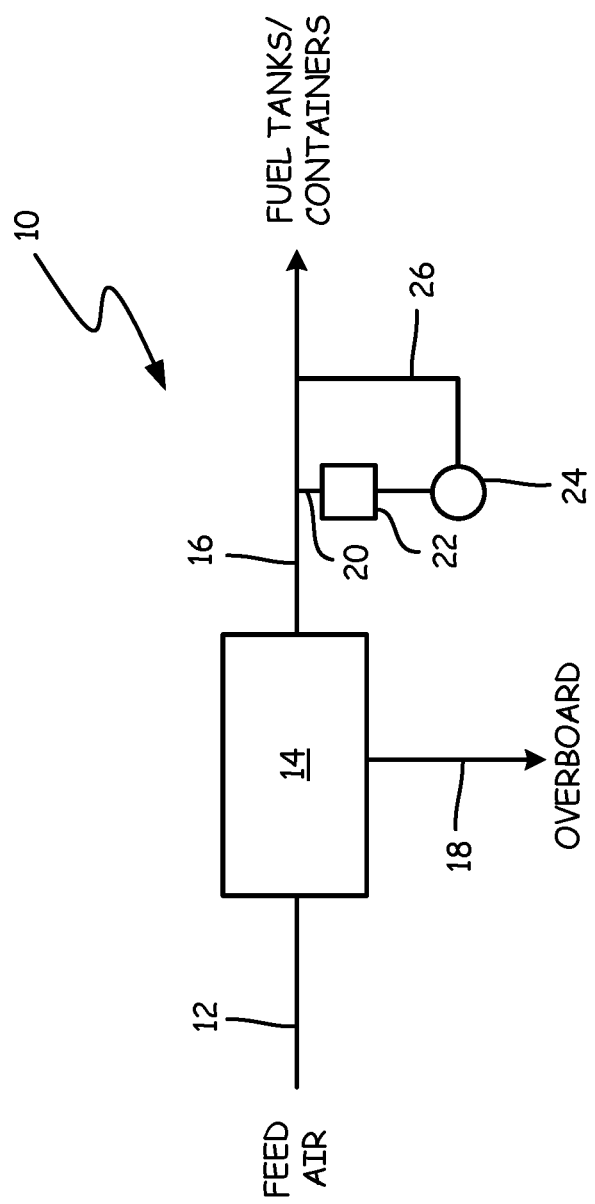
FIG. 1 is a schematic diagram of a nitrogen generation system.

FIG. 1 is a schematic diagram of NGS 10. NGS 10 includes feed air line 12, ASM 14, NEA line 16, OEA line 18, oxygen sensing line 20, gas adsorption filter 22, oxygen sensor 24, and NEA return line 26. ASM 14 receives feed air through feed air line 12 and separates the feed air into NEA and OEA. The NEA leaves ASM 14 through NEA line 16 and is routed to fuel tanks and containers for inerting. The OEA leaves ASM 14 through OEA line 18 and is typically rejected overboard.

A portion of the NEA in NEA line 16 enters oxygen sensing line 20 and flows through oxygen sensing line 20 and gas adsorption filter 22 to oxygen sensor 24. Oxygen sensor 24 determines the concentration of oxygen in the NEA in order to ensure that the oxygen concentration in the NEA remains below a prescribed level. For commercial aircraft, the oxygen concentration in the NEA should remain below 12%. For military aircraft, the oxygen concentration in the NEA should remain below 8%. The oxygen concentration sensed by oxygen sensor 24 can be communicated to a control system. The control system can adjust the flow rate and temperature of feed air flowing through ASM 14 in order to change the oxygen concentration in the NEA to a desired level. In the embodiment shown, once the oxygen concentration in the NEA is determined, the NEA flows back into NEA line 16 through NEA return line 26. This allows most of the NEA generated by ASM 14 to be routed to fuel tanks and containers for inerting. In an alternative embodiment, the NEA flowing through oxygen sensor 24 can be rejected overboard.

Oxygen sensor 24 is susceptible to premature failure due to the presence of siloxane compounds in the NEA passing through oxygen sensor 24. Siloxane compounds can form a silicon dioxide film on top of oxygen sensor 24 and block diffusion of oxygen through oxygen sensor 24. As a result, oxygen sensor 24 cannot be properly calibrated and will not be able to provide an accurate measurement of the oxygen concentration in the NEA. In order to prevent exposure of oxygen sensor 24 to siloxane compounds, gas adsorption filter 22 is used to adsorb the siloxane compounds in the portion of the NEA in oxygen sensing line 20.

In the embodiment shown, gas adsorption filter 22 is independent from oxygen sensor 24. In an alternative embodiment, gas adsorption filter 22 can be an integral part of oxygen sensor 24. Gas adsorption filter 22 has a finite life, so in either embodiment, gas adsorption filter 22 can be removable so that gas adsorption filter 22 easy to replace. In the embodiment shown, gas adsorption filter 22 is placed in a flow through configuration so that the NEA flows through gas adsorption filter 22. Gas adsorption filter 22 includes a sorbent to adsorb the siloxane compounds in the NEA flowing through gas adsorption filter 22. In one embodiment, gas adsorption filter 22 can be a packed bed with activated carbon pellets. In another embodiment, gas adsorption filter 22 can be an activated carbon fiber gas adsorption filter. In other embodiments, gas adsorption filter 22 can include other forms of activated carbon or another sorbent.

As the NEA passes through gas adsorption filter 22, the sorbent of gas adsorption filter 22 adsorbs the siloxane compounds in the NEA and prevents the siloxane compounds from entering oxygen sensor 24. Gas adsorption filter 22 is advantageous, because gas adsorption filter 22 prevents contamination of oxygen sensor 24 with siloxane compounds and thus improves the stability, accuracy, performance, and life of oxygen sensor 24. In the embodiment shown, gas adsorption filter 22 is used in the context of NGS 10. In other embodiments, gas adsorption filter 22 can be used in any system that requires an oxygen sensor that is at risk of exposure to siloxane compounds.

Figure 2:
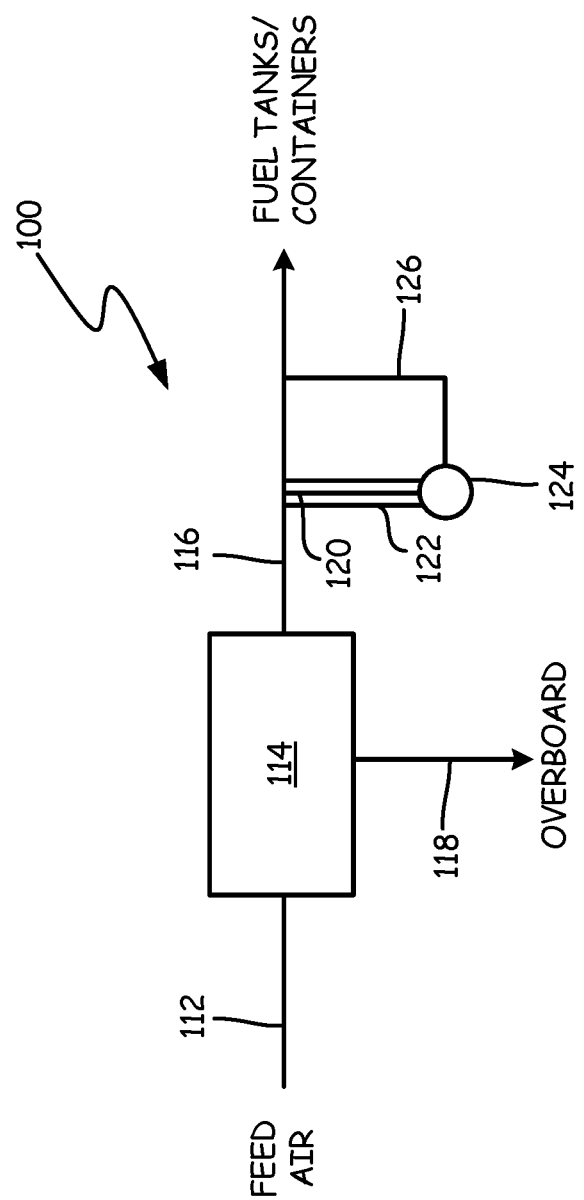
FIG. 2 is a schematic diagram of another embodiment of the nitrogen generation system of FIG. 1.

FIG. 2 is a schematic diagram of NGS 100, another embodiment of NGS 10 of FIG. 1. NGS 100 includes feed air line 112, ASM 114, NEA line 116, OEA line 118, oxygen sensing line 120, protection gas adsorption filter 122, oxygen sensor 124, and NEA return line 126. NGS 100 functions similarly to NGS 10 in FIG. 1. ASM 114 receives feed air through feed air line 112 and separates the feed air into NEA and OEA. The NEA leaves ASM 114 through NEA line 116 and is routed to fuel tanks and containers for inerting. The OEA leaves ASM 114 through OEA line 118 and is typically rejected overboard.

A portion of the NEA in NEA line 116 enters oxygen sensing line 120 and flows through oxygen sensing line 120 and gas adsorption filter 122 to oxygen sensor 124. Oxygen sensor 124 determines the concentration of oxygen in the NEA in order to ensure that the oxygen concentration in the NEA remains below a prescribed level. The oxygen concentration sensed by oxygen sensor 124 can be communicated to a control system. The control system can adjust the flow rate and temperature of feed air flowing through ASM 114 in order to change the oxygen concentration in the NEA to a desired level. In the embodiment shown, once the oxygen concentration in the NEA is determined, the NEA flows back into NEA line 116 through NEA return line 126. This allows most of the NEA generated by ASM 114 to be routed to fuel tanks and containers for inerting. In an alternative embodiment, the NEA flowing through oxygen sensor 124 can be rejected overboard.

Unlike gas adsorption filter 22 in NGS 10, gas adsorption filter 122 is placed in a flow by configuration in oxygen sensing line 120. In the embodiment shown, gas adsorption filter 122 is a coating of a sorbent that covers oxygen sensing line 120. In one embodiment, gas adsorption filter 122 is a coating of activated carbon that covers oxygen sensing line 120. In other embodiments, gas adsorption filter 122 can be a coating of another suitable sorbent such as a porous medium. When the portion of NEA flows through oxygen sensing line to oxygen sensor 124, the NEA flows by gas adsorption filter 122, and gas adsorption filter 122 absorbs the siloxane compounds in the NEA, preventing the siloxane compounds from entering oxygen sensor 124.

Like gas adsorption filter 22 of NGS 10, gas adsorption filter 122 is advantageous, because gas adsorption filter 122 prevents contamination of oxygen sensor 124 with siloxane compounds and thus improves the stability, accuracy, performance, and life of oxygen sensor 124. In the embodiment shown, gas adsorption filter 122 is used in the context of NGS 100. In other embodiments, gas adsorption filter 122 can be used in any system that requires an oxygen sensor that is at risk of exposure to siloxane compounds.

Discussion of Possible Embodiments

The following are non-exclusive descriptions of possible embodiments of the present invention.

An air separation system according to an exemplary embodiment of this disclosure, among other possible things includes an air separation module configured to receive feed air and separate the feed air into nitrogen-enriched air and oxygen-enriched air, a nitrogen-enriched air line for transporting the nitrogen-enriched air from the air separation module to a fuel tank for inerting, an oxygen sensing line connected to the nitrogen-enriched air line, a gas adsorption filter located in the oxygen sensing line, and an oxygen sensor downstream of the gas adsorption filter in the oxygen sensing line.

The air separation system of the preceding paragraph can optionally include, additionally and/or alternatively, any one or more of the following features, configurations and/or additional components:

A further embodiment of the foregoing air separation system, wherein the gas adsorption filter is removable.

A further embodiment of any of the foregoing air separation systems, wherein the gas adsorption filter includes a sorbent.

A further embodiment of any of the foregoing air separation systems, wherein the gas adsorption filter is a packed bed with activated carbon pellets or an activated carbon fiber gas adsorption filter.

A further embodiment of any of the foregoing air separation systems, wherein the gas adsorption filter is integral to the oxygen sensor.

A further embodiment of any of the foregoing air separation systems, wherein the gas adsorption filter is a coating of activated carbon or a porous media on the oxygen sensing line.

A further embodiment of any of the foregoing air separation systems, and further including a nitrogen-enriched air return line connected to the oxygen sensor and the nitrogen-enriched air line.

An oxygen sensor protection system according to an exemplary embodiment of this disclosure, among other possible things includes an oxygen sensing line, a gas adsorption filter located in the oxygen sensing line, and an oxygen sensor downstream of the gas adsorption filter in the oxygen sensing line.

The oxygen sensor protection system of the preceding paragraph can optionally include, additionally and/or alternatively, any one or more of the following features, configurations and/or additional components:

A further embodiment of the foregoing oxygen sensor protection system, wherein the gas adsorption filter is removable.

A further embodiment of any of the foregoing oxygen sensor protection systems, wherein the gas adsorption filter includes a sorbent.

A further embodiment of any of the foregoing oxygen sensor protection systems, wherein the gas adsorption filter is a packed bed with activated carbon pellets or an activated carbon fiber gas adsorption filter.

A further embodiment of any of the foregoing oxygen sensor protection systems, wherein the gas adsorption filter is integral to the oxygen sensor.

A further embodiment of any of the foregoing oxygen sensor protection systems, wherein the gas adsorption filter is a coating of activated carbon or a porous medium on the oxygen sensing line.

A method of protecting an oxygen sensor from siloxane compounds according to an exemplary embodiment of this disclosure, among other possible things includes flowing air through an oxygen sensing line, filtering the air with a sorbent to adsorb siloxane compounds in the air, and flowing the air through an oxygen sensor to sense a concentration of oxygen in the air.

The method of the preceding paragraph can optionally include, additionally and/or alternatively, any one or more of the following features, configurations and/or additional components:

A further embodiment of the foregoing method, wherein the oxygen sensing line is coated with activated carbon such that the air is gas adsorption filtered by the activated carbon when the air flows through the oxygen sensing line.

A further embodiment of any of the foregoing methods, wherein filtering the air includes flowing the air through a packed bed with activated carbon pellets or flowing the air through an activated carbon gas adsorption filter.

A further embodiment of any of the foregoing methods, and further including flowing feed air into an air separation module, separating the feed air into nitrogen-enriched air and oxygen-enriched air in the air separation module, transporting the nitrogen-enriched air from the air separation module to a fuel tank of an aircraft for inerting, and flowing a portion of the nitrogen-enriched air into the oxygen sensing line.

A further embodiment of any of the foregoing methods, and further including transporting the portion of the nitrogen-enriched air to the fuel tank of the aircraft for inerting after the concentration of oxygen is sensed in the portion of the nitrogen-enriched air.

A further embodiment of any of the foregoing methods, and further including rejecting the oxygen-enriched air overboard the aircraft.

While the invention has been described with reference to an exemplary embodiment(s), it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment(s) disclosed, but that the invention will include all embodiments falling within the scope of the appended claims.

The invention claimed is:

1. A method of producing inert gas comprising:
    separating feed air into nitrogen-enriched air and oxygen-enriched air in an air separation module;
    flowing the nitrogen-enriched air from the air separation module down a nitrogen-enriched air line towards a fuel tank for inerting;
    funneling a portion of the nitrogen-enriched air from the nitrogen-enriched air line through an oxygen sensing line to an oxygen sensor;
    removing siloxane compounds from the portion of nitrogen-enriched air in the oxygen sensing line upstream of the oxygen sensor;
    detecting a concentration of oxygen in the portion of the nitrogen-enriched air with the oxygen sensor; and
    returning the portion of the nitrogen-enriched air back to the nitrogen-enriched air line.

2. The method of claim 1, wherein removing siloxane compounds comprises filtering the portion of nitrogen-enriched air with a gas adsorption filter in the oxygen sensing line.

3. The method of claim 2, wherein filtering with a gas adsorption filter comprises removing siloxane compound with a sorbent containing activated carbon.

4. The method of claim 3, wherein filtering the portion of nitrogen-enriched air includes flowing the portion of nitrogen-enriched air through a packed bed with activated carbon pellets.

5. The method of claim 3, wherein the oxygen sensing line is coated with activated carbon such that the portion of nitrogen-enriched air is gas adsorption filtered by the activated carbon when the portion of nitrogen-enriched air flows through the oxygen sensing line.

6. The method of claim 2, wherein the gas adsorption filter is removable from the oxygen sensing line.

7. The method of claim 2, wherein the gas adsorption filter is integral to the oxygen sensor.

8. The method of claim 2, wherein filtering the portion of nitrogen-enriched air and detecting a concentration of oxygen are done simultaneously.

9. The method of claim 1, and further comprising transporting the portion of the nitrogen-enriched air to the fuel tank of the aircraft for inerting after the concentration of oxygen is sensed in the portion of the nitrogen-enriched air.

10. The method of claim 1, and further comprising rejecting the oxygen-enriched air overboard the aircraft.

11. The method of claim 1, wherein the oxygen sensing line is on the nitrogen-enriched air line.

12. The method of claim 1, wherein the oxygen sensor is on the oxygen sensing line.

* * * * *